(12) United States Patent
Invie et al.

(10) Patent No.: US 8,708,141 B1
(45) Date of Patent: Apr. 29, 2014

(54) ULTRAVIOLET SHIELDS FOR EYES AND KIT THEREFOR

(76) Inventors: Ted A. Invie, Beaverton, OR (US); Fred K. Hahn, Oregon City, OR (US)

( * ) Notice: Subject to any disclaimer, the term of this patent is extended or adjusted under 35 U.S.C. 154(b) by 270 days.

(21) Appl. No.: 13/243,540

(22) Filed: Sep. 23, 2011

Related U.S. Application Data

(63) Continuation-in-part of application No. 11/900,288, filed on Sep. 11, 2007, now abandoned.

(51) Int. Cl.
    *B65D 69/00* (2006.01)
(52) U.S. Cl.
    USPC .......................... 206/223; 206/438; 206/363
(58) Field of Classification Search
    USPC .......... 206/570, 572, 223, 363, 438, 440, 803
    See application file for complete search history.

(56) References Cited

U.S. PATENT DOCUMENTS

| | | | |
|---|---|---|---|
| 4,347,284 A | 8/1982 | Tsutomu et al. | |
| 4,502,476 A | 3/1985 | Welt | |
| 4,701,965 A * | 10/1987 | Landis | 2/428 |
| 4,979,811 A * | 12/1990 | Boyer | 351/44 |
| 5,127,423 A | 7/1992 | Draeger | |
| 5,134,025 A | 7/1992 | Zenda et al. | |
| 6,037,280 A * | 3/2000 | Edwards et al. | 442/131 |
| 6,908,195 B2 * | 6/2005 | Fuller | 351/158 |
| 6,923,537 B2 | 8/2005 | Hartley et al. | |

* cited by examiner

*Primary Examiner* — J. Gregory Pickett
*Assistant Examiner* — Raven Collins
(74) *Attorney, Agent, or Firm* — Robert C. Montgomery; Montgomery Patent & Design

(57) ABSTRACT

An eye protection kit comprises a plurality of soft, smooth eye patches and an atomizer providing ultraviolet radiation protection for use while sunbathing or in a tanning bed is herein disclosed stored within a carrying case. The eye patches are each comprised of a textile material comprising reinforced perimeters. For personal comfort and to maintain moisture, the patches are wetted with a cooling fluid therefrom the atomizer. Further, the patches would be oversized, thus providing shielding to areas adjacent to the eye where skin lines often form and shielding below the eyes where sunbathers sometimes develop unflattering skin discolorization.

6 Claims, 4 Drawing Sheets

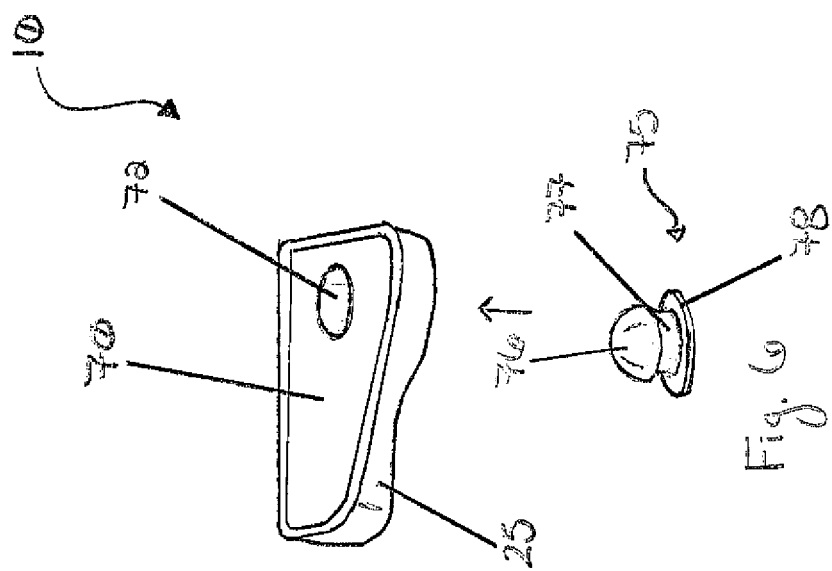
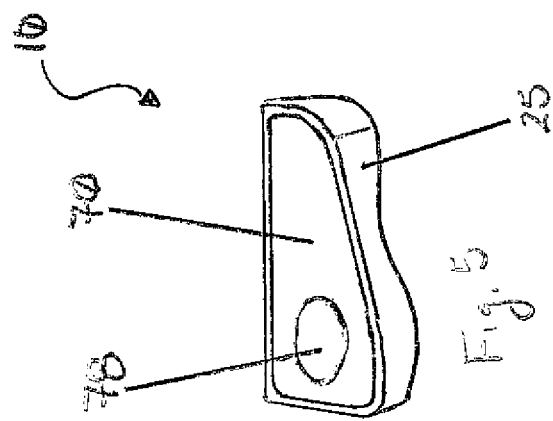
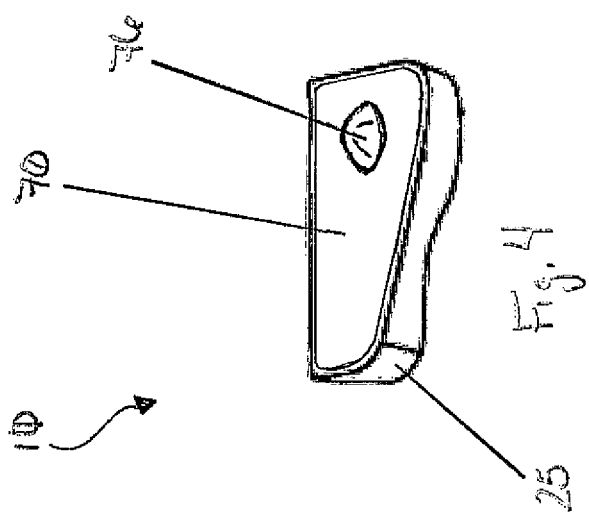

ULTRAVIOLET SHIELDS FOR EYES AND KIT THEREFOR

RELATED APPLICATIONS

The present invention is a continuation-in-part of and claims the benefit of U.S. application Ser. No. 11/900,288, filed Sep. 11, 2007 now abandoned, the entire disclosures of which are incorporated herein by reference.

FIELD OF THE INVENTION

The present invention relates generally to a protective eye patch shields and, more particularly, to said shields having ultraviolet (UV) protection for use while sunbathing or in a tanning bed.

BACKGROUND OF THE INVENTION

Many people enjoy sun bathing in the summer sun, and others enjoy tanning in tanning beds during cold winter months. While these people are often rewarded with a tan, they also risk exposure to eye damage. Such eye damage is not limited to the eye itself from UV damage, but also around the eye. Age lines can become more pronounced when exposed to long periods of UV light. Also, the areas underneath the eyes can become more darkened and mottled, thus giving one the "bags" under the eyes. Some people use sunglasses while sunbathing, which do help somewhat, but may result in the uneven and unwanted tan lines caused by the frames and the size of the glasses. Accordingly, there is a need for a means by which sunbathers and tanning bed users can be protected from eye damage and uneven tanning. The development of the invention herein disclosed fulfills this need.

The protective eye shields is a pair of terry cloth towel eye patches that cover the eye and surrounding area while sunbathing or in a tanning bed. The patches would be made of suitable cloth materials such as, but not limited to, 100% Egyptian cotton permanently treated with ultraviolet radiation protection. The shields may be wetted with distilled water or similar substances to soothe the person's eyes and maintain moistness as well as help the pads conform to the profile of the eye area. The oversize shields would also protect the area around the outer edge of the eye where skin lines typically usually form. Additionally, the shields also cover below the eye where sunbathers sometimes develop darkening and dry skin. The shields can be easily washed between uses. The use of the innovative eye shields with UV radiation protection helps protect a person's eyes and surrounding area while sunbathing or tanning in an efficient, healthful and safe manner.

Several attempts have been made in the past to provide a means to protect one's eyes from harmful UV rays, either from sunbathing or tanning in a bed. U.S. Pat. No. 6,923,537 in the name of Hartley et al. discloses eyewear for ballistic and light protection including a lens capable of being mounted and interchangeable between a plurality of platforms, which may include goggles, spectacles, or the like. Unfortunately, the Hartley et al. design does not provide for a conformable eye shield made of cloth nor does it provide a method for moistening said shields with an atomizer.

U.S. Pat. No. 4,701,965 issued in the name of Landis provides a visor-type mask for dentists, comprising a device that attaches to the head above the eyes and a transparent shield that extends down below the mouth to prevent unwanted splatter from using dentistry handpieces. The shield is detachable for cleaning and replacement and a filter may be applied to the shield for eye protection. Unfortunately, the Landis device differs from the present invention in that it involves a detachable visor shield with an attachable UV filter to the shield, wherein the present invention utilizes a conformable cloth-like shield for direct placement thereon the eye region of the user, which has integral UV protection.

U.S. Pat. No. 4,347,284 issued in the name of Tsutomu et al. describes a white sheet cover material capable of reflecting ultraviolet rays comprising an outer surface of a colorless thermoplastic polymer material and a white ultraviolet ray-reflecting agent. The Tsutomu et al. device is not designed to be manufactured in a user-wearable fashion in the shape and fashion of an eye shield and, as such, does not provide any comfort to a user when worn. Additionally, the use of a wetting agent for the eye shield providing additional comfort to the user and supplied in a kit form.

U.S. Pat. No. 6,037,280 issued in the name of Edwards et al., describes an ultraviolet ray blocking textile containing ultraviolet ray deflecting, absorbing, reflecting, or scattering particles that are bound to the textile via a binding agent. The textile may be in the form of an article of clothing, an umbrella, a tent, or the like. The particles may be applied thereto the fabric before or after manufacturing the textile by immersion or spraying methods. Herein, the Edwards et al. device does not provide specifically for an eye shield made of a soft, conforming material further comprising serged or stitched perimeters for added durability and to prevent unraveling. Additionally, the present invention provides for fine particles to be introduced to the eye shields to reflect ultraviolet ray light and comes in a kit form with an atomizer for wetting said shields to provide additional comfort.

None of the prior art particularly describes a plurality of ultraviolet light reflecting eye shields in the form of oversized patches that conforms to the eye region of a user during sunbathing or tanning in a bed. Said eye shields are available in a kit form with an atomizer for wetting said shields for additional comfort and ultraviolet light reflecting properties. Accordingly, there is a need for a method of utilizing such a device.

SUMMARY OF THE INVENTION

In view of the foregoing disadvantages inherent in the prior art, it has been observed that there is need of a set of eye shields in the form of patches further comprising ultraviolet light reflecting properties, particularly for use during sunbathing or tanning in a bed.

It has further been observed that there is a need for such a set of eye shields to be provided in a kit form also comprising an atomizer for selective wetting of said eye shields.

The object of the present invention is to provide such a set of eye shields, each comprising an overall size and shape of an oversized eye patch to ensure that an eye region of a user is completely covered.

A further object of the present invention is to provide each eye patch with a soft rubberized band located around an outer perimeter thereof, thereby creating durability, preventing unraveling, and providing additional weight to assist in maintaining the position of the eye patch while being worn.

Another object of the present invention provides for said eye patch to be comprised of a soft, smooth material with inherent ultraviolet light reflecting properties such as terry cloth, Egyptian cotton, and a polymer film with or without foamed cell structures which may also include or exclude organic or inorganic particles.

Another object of the present invention provides for said eye patch to be manufactured with fine inorganic or organic particles being added to further reflect ultraviolet light, such as silica particles.

Yet another object of the present invention is to provide such a set of eye patches, each comprising one-half (½) inch to one (1) inch around the side of the eyes where fine lines or "crow's feet" manifestly occur and below the eyes where darker pigmentation typically occurs. Each eye patch 20 comprises particular perimeter features comprising an outer side "A" approximately one-half (½) inch long, a lower curve approximately one and one-half (1½) inches long, a side "B" adjacent to a nose area approximately three-fourths (¾) of an inch long, and a side "C" approximately two and one-half (2½) inches long extending approximately even with and parallel to the eyebrow region.

Yet another object of the present invention is to provide each of the eye patches to comprise an aperture which enables insertion of an insert that covers a user's pupil in order to provide enhanced protection of UVA- and UVB-type radiation to the user.

Yet another object of the present invention is to provide each insert to include a conically-shaped lens with a one-way mirrored surface, a shaft integrally molded to a bottom surface of the lens, and a disc-shaped base integrally molded to the shaft opposite the lens, thereby enabling the lens to be exposed from an upper surface of the eye patch and the base to be exposed upon an exterior bottom surface of the eye patch. The base prohibits the insert from unnecessary or accidental removal.

The object of the present invention is to provide such a set of eye shields available in a kit enclosure therewith an atomizer for wetting the eye shields, thereby providing greater comfort to the user as well as enhancing the ultraviolet light reflecting properties of the eye shields.

Still yet another object of the present invention is to provide such a set of eye shields having a monogram, imprinting, or other decorative insignia thereon an outer surface.

To achieve the above and other objectives, a method of protecting a user's eyes from harmful ultraviolet light radiation comprises the following steps: providing a plurality of eye patches and an atomizer within a kit enclosure; removing a cap therefrom the atomizer; filling the atomizer with fluid/spray, if not already filled; releasing the pair of eye patches and the atomizer therefrom a kit liner; depressing the spray button downwardly to expel the fluid/spray thereon each of two (2) eye patches to achieve a pair of moistened eye patches; placing said moistened eye patches thereon the surrounding area of the user's eyes, thereby covering said eyes; sunbathing or tanning using a tanning bed; removing the eye patches therefrom the user's face; washing said eye patches; storing the eye patches and atomizer therein the kit enclosure until needed; and, benefiting from the comfort of moistened eye patches as well as protection of one's eyes from harmful ultraviolet light while using the present invention during tanning.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 4 is a top perspective view of an alternate eye patch 70, according to an alternate embodiment of the present invention;

FIG. 5 is a bottom perspective view of the alternate eye patch 70, according to the alternate embodiment of the present invention; and, FIG. 6 is an exploded perspective view of the alternate eye patch 70 depicting an insert 75, according to the alternate embodiment of the present invention.

Figure 1:
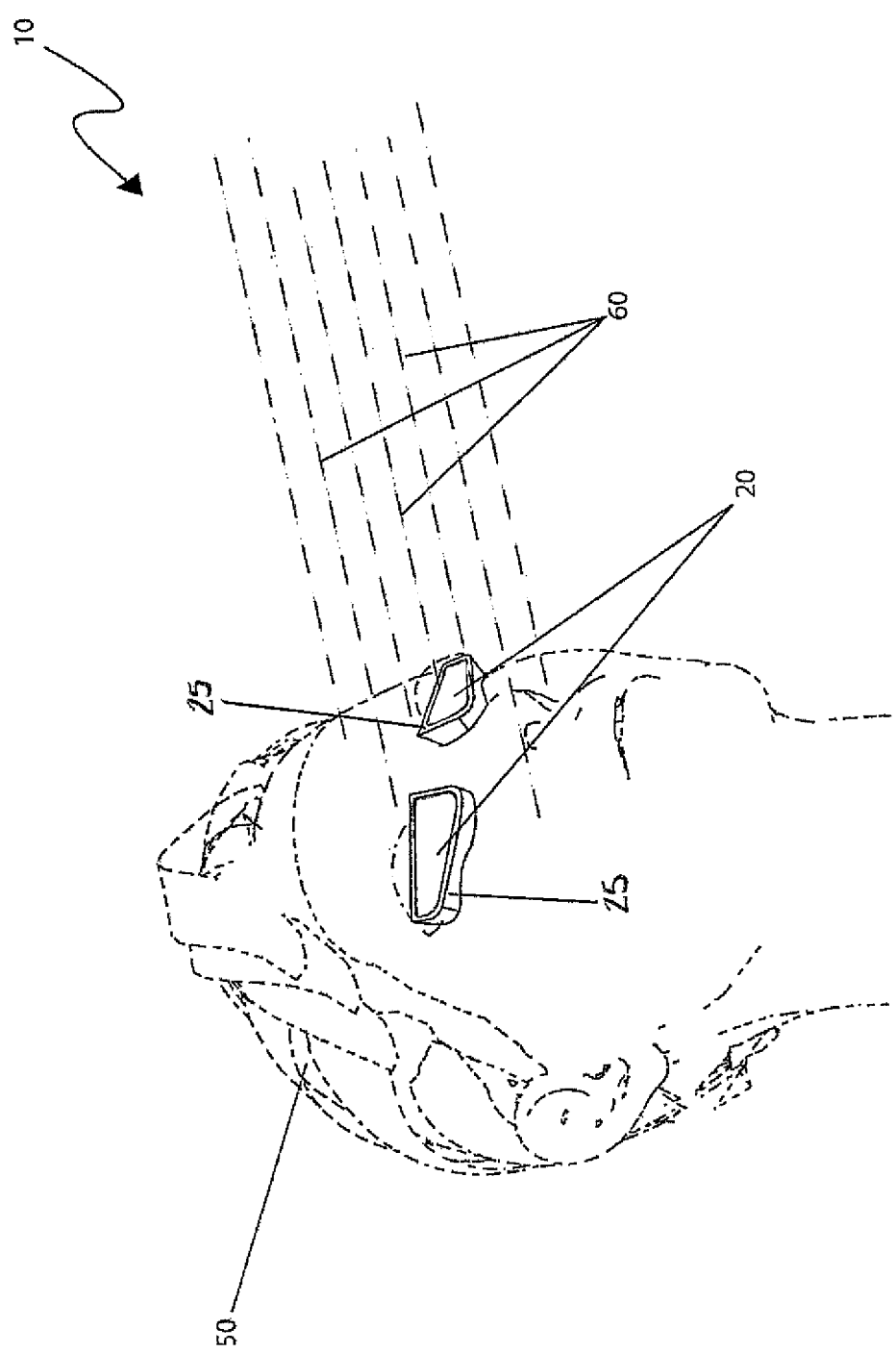
FIG. 1 is an environmental view of ultraviolet shields for eyes 10 depicting an in-use state, according to a preferred embodiment of the present invention; and, FIG. 2 is a close-up view of ultraviolet shields for eyes 10, according to a preferred embodiment of the present invention.

DESCRIPTIVE KEY 10 ultraviolet shields for eyes
20 eye patch
21 side "A"
22 side "B"
23 curve
24 side "C"
25 band
30 atomizer
33 spray button
34 cap
35 fluid/spray
40 kit enclosure
41 kit base
42 kit liner
43 kit lid
50 user
60 ultraviolet light
70 alternate eye patch
72 aperture
75 insert
76 lens
77 shaft
78 base

DETAILED DESCRIPTION OF THE PREFERRED EMBODIMENT

Figure 2:
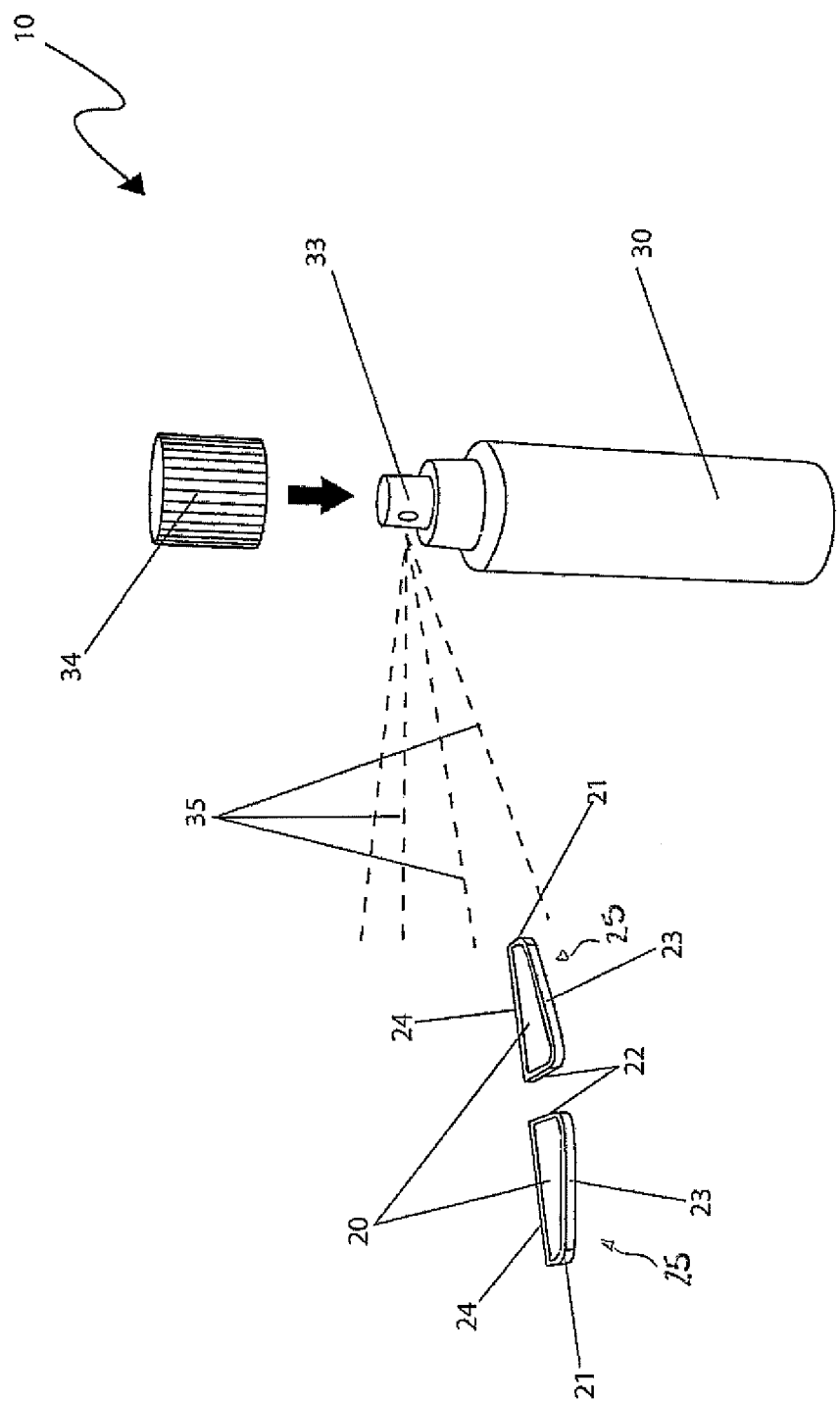
Figure 3:
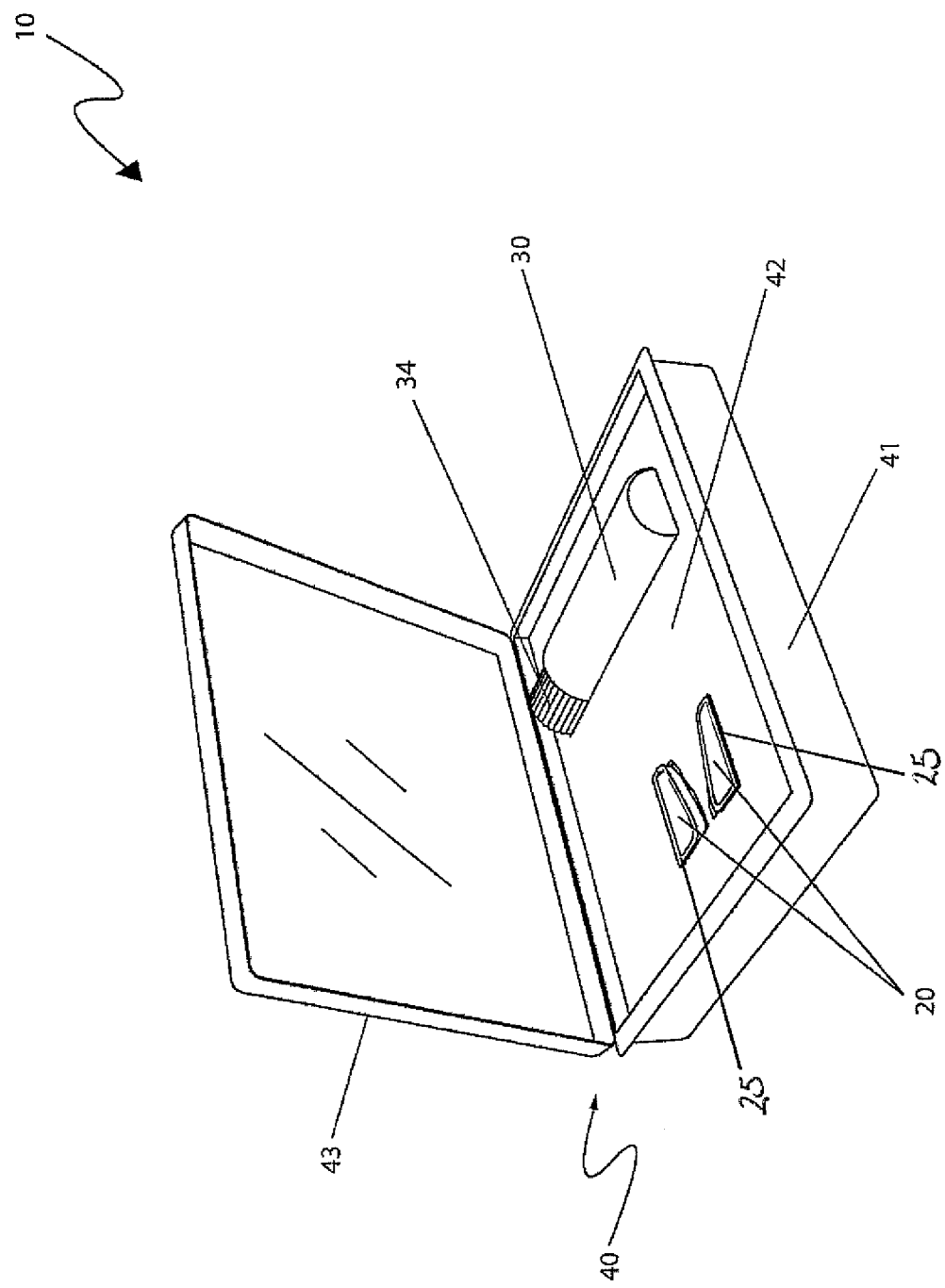
FIG. 3 is a perspective view of a kit 40 for said ultraviolet shields for eyes 10, according to a preferred embodiment of the present invention.

The best mode for carrying out the invention is presented in terms of its preferred embodiment, herein depicted within FIGS. 1 through 3. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a system and method for ultraviolet shields for eyes (herein described as the "system") 10 comprising a kit enclosure 40, a plurality of soft smooth eye patches 20 having ultraviolet light 60 protection, and a moisturizing atomizer 30, particularly for use while sunbathing or in a tanning bed. The construction of the eye patch portion 20 of the invention 10 would be made of a textile material with serged perimeters. For personal comfort and to maintain moisture 35, the patches 20 may be wetted. Furthermore, the patches 20 would be oversized, thus providing shielding to areas adjacent to the eye region where skin lines often form.

Referring now to FIG. 1, an environmental view of the system 10 depicting an in-use state, according to the preferred embodiment of the present invention, is disclosed. The system 10 is illustrated here depicting an application to a user's eye region 50 providing an ultraviolet light 60 protection means to the eyes. The system comprises a plurality of oversized patches 20 providing shielding to areas adjacent to the eye where skin lines and skin discolorization often form. The patches 20 comprise of ovular-shaped thick textile appliances providing a perimeter approximately two (2) to three (3) inches long and one (1) inch wide.

Referring now to FIG. 2, a close-up view of the system 10 according to the preferred embodiment of the present invention, is disclosed. The system 10 comprises a plurality of soft, lightweight, smooth eye patches 20 providing ultraviolet light 60 protection for use while sunbathing or in a tanning bed. The eye patches 20 comprise an ultraviolet light-reflecting fabric providing excellent moisture permeability thereby permitting moistening or dampening of said eye patches 20 without becoming too hot even when exposed to said ultraviolet light 60. The eye patches 20 are envisioned being made using ultraviolet light-reflecting materials such as pure thick cotton, a polymer film with or without foamed cell structures which may also include or exclude organic or inorganic particles, or the like. Furthermore, the eye patches 20 are envisioned to comprise fine inorganic or organic particles, such as silica particles, being added in a proper ratio to the eye patches 20 to further reflect ultraviolet light 60, thereby reflecting light in the ultraviolet ray wavelength region. The perimeter of the eye patches 20 is to be encompassed with a soft rubberized band 25, thereby creating durability and preventing unraveling. The band 25 also provides additional weight to assist in maintaining the position of the system 10 while upon the user 50. The eye patches 20 are envisioned to be ovular-shaped and formed to fit the general contours of the shape of a user's eyes 50 in a size that fits all the curvatures of the eye region where fine lines usually form, including the eyelid and under-eye areas. The eye patches 20 are preferably, but not essentially, one-half (½) inch to one (1) inch around the side of the eyes where fine lines or "crow's feet" manifestly occur and below the eyes where darker pigmentation typically occurs. Each eye patch 20 comprises particular perimeter features comprising a side "A" 21, a curve 23, a side "B" 22, and a side "C" 24. The side "A" portion 21 of the eye patch 20, along an outer side, is approximately one-half (½) inch long before the curve 23, which is located along a lower edge and envisioned to be approximately one and one-half (1½) inches long. The curve 23 curves upwardly towards the eyelid and eyebrow area toward side "B" 22, being located toward and closest to the nose area envisioned to be three-fourths (¾) of an inch long intersecting with the side "C" 24 at the top of said eye patch 20 being two and one-half (2½) inches long extending approximately even with and parallel to the eyebrow region. The eye patches 20 are envisioned to be oversized with regards to the eye socket thus providing shielding to both the eyes 50 and adjacent areas to the eyes 50 where skin lines and discoloration often form; however, the eye patches 20 may be introduced in a plurality of sizes proportional to the preferred embodiment to fit various sized eye areas covering the iris, cornea, retina, and surrounding areas adjacent to the eyes 50. The eye patches 20 are envisioned to be cleansed therebetween uses. The eye patches 20 are further envisioned being introduced in a variety of colors and patterns and providing fashionable monograms, personalized logos, initials, slogans, marketable labeling, and/or other aesthetically pleasing motifs.

The system 10 further comprises a common commercially available plastic atomizer 30 comprising a one (1) to two (2) ounce fluid capacity containing cooling fluids therein such as, but not limited to, distilled water, purified water, tap water, or bottled water. The atomizer comprises a cap 34 and a spray button 33 which provides a fluid/spray 35 in an expected manner to wet or dampen the eye patches 20 to the user's 50 liking, thereby providing personal comfort while maintaining moisture to the eye area. The atomizer 30 may comprise indentations or recessed finger sections along the partial or entire span used as grips shaped to accommodate a user's hand 50. The atomizer 30 defines an interior compartment for housing said cooling fluid/spray 35 with an open top portion leading toward a spray button 33. In an expected manner, an internal elongated tube is in fluid communication with said spray button 33 operable such that it resides in said interior compartment of the atomizer 30 utilizing hydraulic pressure to regulate the cooling fluid/spray 35 thereto the spray button 33. The spray button 33 provides a regulating means thereto the fluid/spray 35 via a dispersing aperture when depressed downwardly in a normal fashion.

The moistening of the eye patches 20 not only moistens and soothes the outer epidermis and eyes but also helps to relax and conform said eye patches 20 to the profile of a user's eye region 50, thereby sealing out ultraviolet light 60.

Referring now to FIG. 3, a perspective view of the system 10 depicting a kitted state, according to the preferred embodiment of the present invention, is disclosed. The system 10 comprises a rectangular-shaped plastic kit enclosure 40 which provides a protective packaging means to the system 10 therein. The kit enclosure 40 is envisioned to be approximately four (4) to six (6) inches wide by approximately two (2) inches deep further comprising an opaque kit base 41 and a transparent kit lid 43 being made using a plastic vacuum or injection molding process. Said kit base 41 is envisioned to be introduced in a variety of decorative colors and patterns. The base 41 and lid 43 comprise an attachment means thereto one another preferably using an integrally molded hinge along a rear edge and molded-in snap-type fastening features located along a front edge; however, said hinging and fastening functions may be provided using common plastic or metal fittings mounted along said perimeter edges using common components found in similar plastic enclosures. The kit base portion 41 comprises an interior urethane foam kit liner 42 providing form-fitting cutouts, thereby providing snug relief areas to the eye patches 20 and atomizer 30 contained therein. The kit liner 42 is envisioned to be sized to accommodate various sizes and shapes of eye patches 20 and atomizers 30 respectively. The eye patches 20 are depicted here being provided as a pair of devices 20 for illustration sake; however, said eye patches 20 may be provided in any number therein said kit 40 and as such should not be interpreted as a limiting factor of the invention 10.

Referring now to FIG. 4, a top perspective view of the alternate eye patch 70, FIG. 5, a bottom perspective view of the alternate eye patch 70, and FIG. 6, an exploded perspective view of the alternate eye patch 70 depicting the insert 75, according to the preferred embodiment of the present invention, is disclosed. Alternately, an alternate eye patch 70 can be utilized to provide enhancing features to the system 10. Although a single alternate eye patch 70 is depicted herein it is known that a pair should be utilized. The alternate eye patch 70 includes an aperture 72 which enables insertion of an insert 75. The insert 75 provides additional UVA and UVB protection to the user 50. The insert 75 includes a lens 76, a shaft 77, and a base 78. The lens 76 is preferably comprised of a conically-shaped UV protected polymer with a one (1) way mirrored surface. A bottom surface of the lens 76 is integrally molded to the tubular shaft 77. The shaft 77 extends through the alternate eye patch 70 in order for the lens 76 to be exposed from an upper surface and the disc-shaped base 78 to be exposed upon an exterior bottom surface of the alternate eye patch 70. The base 78 prohibits the insert 75 from unnecessary or accidental removal. When the alternate eye patch 70 is placed upon a user 50 the insert 75 should cover the users 50 pupil region.

It is envisioned that other styles and configurations of the present invention can be easily incorporated into the teachings of the present invention, and only one particular configuration shall be shown and described for purposes of clarity and disclosure and not by way of limitation of scope. The preferred embodiment of the present invention can be utilized by the common user in a simple and effortless manner with little or no training. Likewise, children, teenagers, men, and/or women alike can find this invention 10 to greatly aid them in protecting eyes and surrounding areas. When the system 10 is first procured it should comprise a lid enclosure 40, two (2) or more eye patches 20, and an atomizer 30. After initial purchase or acquisition of the system 10, it would be prepared and installed as indicated in FIGS. 1 and 2.

The method of utilizing the system 10 may be achieved by performing the following steps: filling the atomizer 30 with fluid/spray 35, if not already filled; releasing the pair of eye patches 20 and the atomizer 30 therefrom the kit liner 42; removing the cap 34 therefrom the atomizer 30; depressing the spray button 33 downwardly to expel the fluid/spray 35 thereon each of the two (2) eye patches 20; placing moistened eye patches 20 thereon the surrounding area of the user's eyes 50, thereby covering said eyes 50; sunbathing or tanning using a tanning bed; removing the eye patches 20 therefrom the user's face 50; washing said eye patches 20; storing the eye patches 20 and atomizer 30 therein the kit enclosure 40 until needed; and, benefiting from the comfort of moistened eye patches 20 as well as protection of one's eyes from harmful ultraviolet light 60 while using the present invention 10 during tanning.

The method of utilizing the system 10 with the alternate eye patch 70 may be achieved by performing the following steps: filling the atomizer 30 with fluid/spray 35, if not already filled; releasing the pair of alternate eye patches 70 and the atomizer 30 therefrom the kit liner 42; removing the cap 34 therefrom the atomizer 30; depressing the spray button 33 downwardly to expel the fluid/spray 35 thereon each of the two (2) alternate eye patches 70; inserting the inserts 75 into the aperture 72 of each alternate eye patch 70; placing moistened alternate eye patches 70 thereon the surrounding area of the user's eyes 50, thereby covering said eyes 50; sunbathing or tanning using a tanning bed; removing the alternate eye patches 70 therefrom the user's face 50; removing the inserts 75 from the alternate eye patches 70; washing said alternate eye patches 70; storing the alternate eye patches 70 and atomizer 30 therein the kit enclosure 40 until needed; and, benefiting from the comfort of moistened alternate eye patches 70 as well as protection of one's eyes from harmful ultraviolet light 60 while using the present invention 10 during tanning.

The system 10 is envisioned to protect the user's eyes 50 from sunlight and other forms of light carrying ultraviolet light 60. The system 10 prevents damage from ultraviolet light 60 not limited to the eye itself, but also includes the delicate areas around the eyes thereby preventing sagging and dropping eyelids, as well as fine lines and pigmentation damage.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A means for shielding an eye region and adjacent areas of a user from harmful ultraviolet light radiation while sunbathing or tanning comprising a plurality of eye patches comprised of ovular-shaped appliances, with each patch further comprising:
    an ultraviolet light-reflecting material;
    an outer side "A";
    a lower curvilinear side;
    an inner side "B";
    an upper side "C";
    a plurality of fine particles to further reflect ultraviolet light radiation;
    an aperture for receiving an insert, further comprising:
        a conically-shaped lens, exposed from an upper surface of each patch, having a one-way mirrored surface;
        a shaft integrally molded to a bottom surface of said lens; and,
        a disc-shaped base integrally molded to said shaft opposite said lens and exposed from an exterior bottom surface of each patch; and,
    wherein said insert inserted into said aperture is located in a central location of each of said plurality of eye patches;
    wherein said insert provides enhanced protection of UVA- and UVB-type radiation;
    wherein said base prohibits said insert from unnecessary or accidental removal;
    wherein each of said plurality of eye patches further comprises a rubberized band located at an outer perimeter thereof;
    wherein each of said plurality of eye patches is oversized with regards to said eye region and adjacent areas thus providing shielding to said eye region where skin lines and discoloration often form; and,
    wherein said rubberized band enhances durability and, prevents unraveling, and maintains a position of a utilized eye patch on said eye region.

2. The means of claim 1, wherein each of said plurality of eye patches comprise either a polymer film with or without foamed cell structures or pure thick Egyptian cotton.

3. The means of claim 1, wherein said plurality of fine particles are silica.

4. The means of claim 1, wherein each of said plurality of eye patches further comprise of the following dimensions:
    said side "A" is approximately one-half inch long;
    said curvilinear side is approximately one and one-half inches long;

said side "B" is approximately three-fourths of an inch long; and, said side "C" is approximately two and one-half inches.

5. The means of claim 4, wherein said plurality of eye patches further comprise both a left eye configuration and a right eye configuration.

6. The means of claim 4, wherein said each of plurality of eye patches further comprise decorative indicia such as the following list: fashionable monograms, personalized logos, initials, slogans, and marketable labeling.

\* \* \* \* \*